(12) United States Patent
Nutten et al.

(10) Patent No.: US 9,498,502 B2
(45) Date of Patent: Nov. 22, 2016

(54) PREVENTION AND TREATMENT OF ALLERGIC DIARRHEA

(75) Inventors: Sophie Nutten, Lausanne (CH); Annick Mercenier, Bussigny (CH); Swantje Duncker, Lausanne (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 13/319,646

(22) PCT Filed: May 7, 2010

(86) PCT No.: PCT/EP2010/056292
§ 371 (c)(1),
(2), (4) Date: Jan. 12, 2012

(87) PCT Pub. No.: WO2010/130661
PCT Pub. Date: Nov. 18, 2010

(65) Prior Publication Data
US 2012/0183506 A1    Jul. 19, 2012

(30) Foreign Application Priority Data
May 11, 2009    (EP) .................................... 09159932

(51) Int. Cl.
*A61K 48/00* (2006.01)
*A61K 35/745* (2015.01)
*A23L 2/52* (2006.01)

(52) U.S. Cl.
CPC ................ *A61K 35/745* (2013.01); *A23L 2/52* (2013.01); *A23L 33/135* (2016.08); *A23V 2002/00* (2013.01)

(58) Field of Classification Search
CPC ........................................ A61K 33/66–35/748
USPC ....................................................... 424/93.4
See application file for complete search history.

(56) References Cited

U.S. PATENT DOCUMENTS

| | | | |
|---|---|---|---|
| 4,332,790 A | 6/1982 | Sozzi et al. | |
| 5,902,578 A * | 5/1999 | Halpin-Dohnalek | A23L 1/0345 424/93.3 |
| 2011/0287143 A1* | 11/2011 | Gysler | A23C 9/127 426/62 |

FOREIGN PATENT DOCUMENTS

| EP | 2251021 | 11/2010 | | |
|---|---|---|---|---|
| FR | 2443247 | 7/1980 | | |
| JP | 1242532 | 9/1989 | | |
| NL | WO 2008153377 A1 * | 12/2008 | ............... | A23L 1/09 |
| WO | 2008153377 | 12/2008 | | |
| WO | WO 2008153377 A1 * | 12/2008 | | |

OTHER PUBLICATIONS

University of Wisconsin Integrative Medicine Department of Family Medicine. Probiotics and Prebiotics: Frequently Asked Questions. 2008. pp. 1-5. Downloaded from the University of Wisconsin Integrative Medicine website: <www.fammed.wisc.edu/integrative>.*
Yasui H. et al.: "Immunomodulatory function of lactic acid bacteria"; Antoine Van Leeuwenhoek, vol. 76, 1999, pp. 383-389, XP002538609;.
He F et al.: "Comparison of mucosal adhesion and species identification of bifidobacteria isolated from healthy and allergic infants"; Fems Immunology and Medical Microbiology, vol. 30, 2001, pp. 43-47, XP002538610.
Marteau P R: "Probiotics in Clinical Conditions"; Clinical Reviews in Allergy and Immunology, vol. 22, No. 3, Jan. 1, 2002, pp. 255-273, XP009027205.
Thibault H et al: "Effects of Long-Term Consumption Of A Fermended Infant Formula (with bifodobacterium Breve C50 and Streptococcus Thermophilus 065) On Acute Diarrhea in Healthy Infants"; Journal of Pediatric Gastroenterology and Nutrition, vol. 39, No. 2, Aug. 1,2004, pp. 147-152, XP009043383.
PCT International Search Report for International Application No. PCT/EP2010056292 with a Date of mailing of Jun. 18, 2010, 4 pages.
Written Opinion of the International Searching Authority on International Application No. PCT/EP2010056292 with a Date of mailing of Jun. 18, 2010, 7 pages.
Saavedra et al., "Feeding of Bifidobacterium bifidum and Streptococcus thermophilus to infants in hospital for prevention of diarrhoea and shedding of rotavirus," The Lancet, (1994) 344.8929: 1046-1049.
Gibson et al., (1995) "Dietary Modulation of the Human Colonic Microbiota: Introducing the Concept of Prebiotics" J. Nutr 125:1401-1412.
Salminen et al., (1999) "Probiotics: how should they be defined,"Trends Food Sci. Technol., 10(3) : 107-110.
Brandt et al, "Mast cells are required for experimental oral allergen-induced diarrhea." Journal of Clinical Investigation, (2003) 112.11: 1666-1677.
Article 2 of the European Commission Directive 2006/141/EC of Dec. 22, 2006, Official Journal of the European Union, Dec. 30, 2006, pp. L401/1-L401/33.
Rona et al., "The prevalence of food allergy: a meta-analysis," Journal of Allergy and Clinical Immunology, (2007) 120.3: 638-646.
Discussion about Allergic Diarrhea, News from People's Daily Online, Feb. 9, 2007 (translation).

* cited by examiner

*Primary Examiner* — Scott Long
*Assistant Examiner* — Nghi Nguyen
(74) *Attorney, Agent, or Firm* — K&L Gates LLP

(57) ABSTRACT

*Bifidobacterium breve* CNCM I-3865 (NCC2950), a composition comprising *Bifidobacterium breve* CNCM I-3865 (NCC2950), and the use of *Bifidobacterium breve* CNCM I-3865 (NCC2950) in the prevention or treatment of allergic diarrhoea are provided. The *Bifidobacterium breve* CNCM I-3865 (NCC2950) can be in a non-replicating form and can be administered to at least partially treat allergic diarrhoea or at least partially reduce the risk of developing allergic diarrhoea.

16 Claims, 1 Drawing Sheet

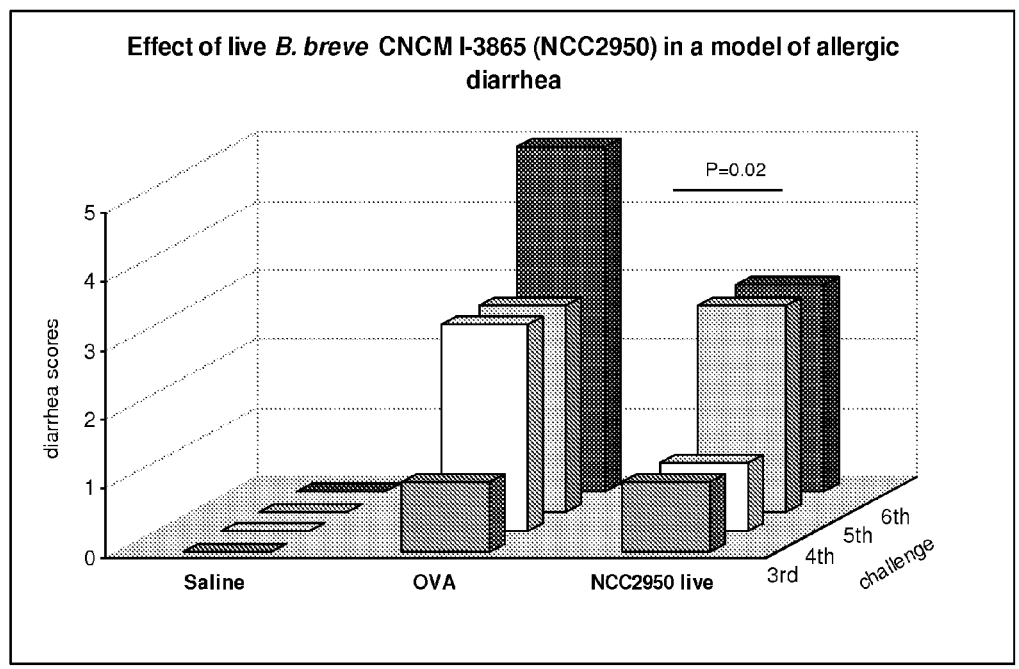

PREVENTION AND TREATMENT OF ALLERGIC DIARRHEA

CROSS REFERENCE TO RELATED APPLICATIONS

The present application is a National Stage of International Application No. PCT/EP2010/056292, filed on May 7, 2010, which claims priority to European Patent Application No. 09159932.4, filed on May 11, 2009, the entire contents of which are being incorporated herein by reference.

This invention relates to the prevention and treatment of allergic diarrhoea.

BACKGROUND OF THE INVENTION

To this day diseases causing diarrhoea remain major global health threats. Diarrhoea severely influences the quality of life of patients all over the world and may pose a particular threat to the survival of infants and children as well as the elderly and patients lacking the means to compensate dehydration and a severe loss of minerals.

As such, acute diarrhoea is a common cause of death in developing countries and the second most common cause of infant deaths worldwide. It causes an estimated 5 million deaths in children under 5 years of age. The cost of management of diarrhoea is a major drain on increasingly burdened healthcare budgets.

Diarrhoea can have a number of different causes such as infection—which comprises diarrhoea caused by rotavirus—, inflammation, allergy and nutritional imbalance resulting it the most common types of diarrhoea including for example secretory diarrhoea, osmotic diarrhoea and motility-related diarrhoea. If the diarrhoea can not be treated by causative means for example by eradication of the pathogen, the type of diarrhoea rather than the underlying cause dictates the symptomatic treatment.

In the last few decades, the use of probiotic bacteria has gained considerable attention as a safe and accessible form of treatment for gastrointestinal diseases. Probiotics were successfully used for the management of diarrhoea caused by viral infections for example with rotavirus. Bacteria that have been employed for intervention in cases of diarrhoea of viral origin belong to the genera *Lactobacillus* and *Bifidobacterium*. The therapeutic capacity of certain probiotic bacteria against rotavirus-induced gastroenteritis has been attributed to their ability to stabilise and reinforce the mucosal barrier, the production of antimicrobial substances and the stimulation of the local antigen-specific and non-specific immune responses. Significant differences have been noted with regard to the effectiveness and mode of action of different strains.

For example, in the early 1990's, Saavedra et al observed that administration of a combination of *Bifidobacterium lactis* and *Streptococcus thermophilus* reduced the incidence of diarrhoea and rotavirus shedding in 29 children followed over 18 months in a chronic care ward in a US hospital (Saavedra et al, The Lancet 344, 1046; 1994). However, less clear results have been obtained in other trials using Bifidobacteria (Thibault et al, J Ped Gastro Nutr 39, 147; 2004).

More recently, it was discovered that *Bifidobacterium breve* CNCM I-3865 (NCC2950) can be used to treat or prevent diarrhoea caused by rotaviral infection (EP 08172263.9).

Other than in rotavirus-induced diarrhoea—where the symptoms are caused by a pathogen—people that suffer from allergic diarrhoea, in particular food allergy, may react to certain foods as if they were laxatives.

Food allergies represent a significant health problem of our society today. They affect all age groups, but in particular children. Around 6 to 8 percent of all children suffer from at least one food allergy. Adults are slightly less affected than children, but still around 4 percent of all adults suffer from food allergies.

Additional to patients with confirmed food allergy there is a large number of people, up to 35%, suffering from hypersensitivity to one or more food allergens (Rona, R. J. et al., 2007, J. Allergy Clin. Immunol. 120: 638-646).

Prolonged allergic diarrhoea may weaken a patient, cause serious dehydration and loss of minerals, such as for example potassium, and may render the supplementation of the body with all necessary nutritional compounds difficult.

Allergic diarrhoea is usually treated today by avoidance of the food allergen and/or symptomatic by rehydration and mineral uptake, which might pose a considerable disturbance of quality of live and cost to the health care system. It would, therefore, be desirable to have available a composition, that allows to prevent the occurrence of allergic diarrhoea and/or treat allergic diarrhoea and which is safe to be administered without side effects, and consequently may be incorporated into food products.

From the foregoing, it may seen that there remains a need for compositions with effective anti-allergic diarrhoea activity and which are suitable for incorporation into products for consumption by infants and young children, for example.

It was consequently the object of the present invention to improve the state of the art and to provide the art with a composition that satisfies these needs.

SUMMARY OF THE INVENTION

The present inventors have surprisingly found that *Bifidobacterium breve* CNCM I-3865 (NCC2950) achieves the object of the present invention.

As it is more and more emerging, a specific health benefit of probiotic bacteria is usually not something that can be predicted on the basis of bacterial species.

More specifically, the present inventors have discovered that a particular strain of *Bifidobacterium breve* originally isolated from human milk, *B. breve* CNCM I-3865 (NCC2950), is highly effective in the prevention and treatment of allergic diarrhoea. Interestingly, it retains this activity even when in a non-replicating form.

*Bifidobacterium breve* CNCM I-3865 (NCC2950) was deposited with the COLLECTION NATIONALE DE CULTURES DE MICROORGANISMES, INSTITUT PASTEUR, 25 rue du Docteur Roux, F-75724 PARIS Cedex 15, under the Budapest treaty on Nov. 15, 2007.

Notably, *Bifidobacterium breve* CNCM I-3865 (NCC2950) was also shown to be active against diarrhoea caused by rotaviral infection.

Hence, *Bifidobacterium breve* CNCM I-3865 (NCC2950) is an exceptional compound that is active in treating or preventing diarrhoea of different causes, namely allergic and rotaviral diarrhoea.

Accordingly, in a first aspect, the present invention provides a composition comprising *Bifidobacterium breve* CNCM I-3865 (NCC2950) for treating or preventing allergic diarrhoea.

In a second aspect, the present invention provides the use of *Bifidobacterium breve* CNCM I-3865 (NCC2950) in the manufacture of a composition for the prevention or treatment of allergic diarrhoea.

In a third aspect, the present invention provides a method of prevention or treatment of allergic diarrhoea comprising administration to a subject in need thereof a therapeutic amount of *Bifidobacterium breve* CNCM I-3865 (NCC2950).

To test the in vivo effect of *Bifidobacterium breve* CNCM I-3865 (NCC2950) in prevention of allergic diarrhea a mouse model of allergic diarrhea was used (Brandt E. B et al. JCI 2003; 112(11): 1666-1667). Following sensitization (2 intraperitoneal injections of Ovalbumin (OVA) and aluminium potassium sulphate at an interval of 14 days; days 0 and 14) male Balb/c mice were orally challenged with OVA for 6 times (days 27, 29, 32, 34, 36, 39) resulting in transient clinical symptoms (diarrhoea) and changes of immune parameters (plasma concentration of total IgE, OVA specific IgE, mouse mast cell protease 1). *Bifidobacterium breve* CNCM I-3865 (NCC2950) was administered by gavage 4 days prior to OVA sensitization (days −3, −2, −1, 0 and days 11, 12, 13 and 14) and during the challenge period (days 23 to 39) in a daily bacterial dose of around $10^9$ colony forming units (cfu)/mouse.

BRIEF DESCRIPTION OF THE DRAWINGS

FIG. 1 shows the median diarrhea scores observed in OVA-sensitized mice challenged either with saline or OVA or challenged with OVA following treatment with live *Bifidobacterium breve* CNCM I-3865 (NCC2950). (Median±RobustSD; $3^{rd}$ challenge: Saline=0±0; OVA=1±1.19; NCC2950 live=1±0; $4^{th}$ challenge: Saline=0±0, OVA=3±1.19; NCC2950 live=1±1.19; $5^{th}$ challenge: Saline=0±0, OVA=3±1.19; NCC2950 live=3±1.19; $6^{th}$ challenge: Saline=0±0, OVA=5±0.6; NCC2950 live=3±0).

DETAILED DESCRIPTION OF THE INVENTION

Since children or infants are in particular affected by food allergies, the composition of the present invention may be intended for children and/or infants. According to the definitions appearing in Article 2 of the European Commission Directive 2006/141/EC of 22 Dec. 2006 on infant formulae and follow-on formulae "Infants" are children under the age of 12 months and young children are children between 1 and 3 years of age.

The term "children" comprises the age groups from 1 to 14 years.

Of course, the compositions of the present invention may also be used for teenagers (15-17 years) or adults (18 years or older).

"Probiotic" means microbial cell preparations or components of microbial cells with a beneficial effect on the health and well-being of the host (Salminen S, Ouwehand A. Benno Y. et al "Probiotics: how should they be defined" Trends Food Sci. Technol. 1999:10 107-10).

All percentages are by weight unless otherwise stated.

The compositions of the present invention may be administered to any subject in need thereof.

These subjects may be humans or may be animals, in particular pet animals. The subjects may belong to any age group, for example to infants, young children, children, teenagers or adults.

The compositions of the present invention comprise *Bifidobacterium breve* CNCM I-3865 (NCC2950) in an amount sufficient to at least partially treat allergic diarrhoea. An amount adequate to accomplish this is defined as "a therapeutically effective dose". Amounts effective for this purpose will depend on a number of factors known to those of skill in the art such as the severity of the disease and the weight and general state of the consumer and the effect of the composition matrix.

In prophylactic applications, *Bifidobacterium breve* CNCM I-3865 (NCC2950) is administered to a consumer susceptible to or otherwise at risk of allergic diarrhoea in an amount that is sufficient to at least partially reduce the risk of developing allergic diarrhoea. Such an amount is defined to be "a prophylactic effective dose". Again, the precise amounts depend on a number of patient specific factors such as the patient's state of health and weight and the effect of the composition matrix.

Those skilled in the art will be able to adjust the therapeutically effective dose and/or the prophylactic effective dose appropriately.

In general the composition of the present invention contains *Bifidobacterium breve* CNCM I-3865 (NCC2950) in a therapeutically effective dose and/or in a prophylactic effective dose.

The probiotic *Bifidobacterium breve* CNCM I-3865 (NCC2350) may be administered to the subject as a composition, for example as a daily dose equivalent to $10^8$ cfu. To infants it may be conveniently administered in an infant feeding formula, a follow-on formula or a growing up milk.

Typically, the *Bifidobacterium breve* CNCM I-3865 (NCC2950) may be administered in an amount equivalent to between $10^3$ and $10^{12}$ cfu/g (dry weight basis), more preferably between $10^7$ and $10^{11}$ cfu/g.

The expression "amount equivalent to" includes the possibilities that the bacteria are live, non-replicating or dead. In other words, the quantity of bacteria is expressed in terms of the colony forming ability of that quantity of bacteria as if all the bacteria were alive irrespectively of whether they are, in fact, alive, non-replicating or dead, or a mixture of any or all of these states.

In one embodiment of the present invention, at least 95%, even more preferably at least 99%, even more preferred all of the *Bifidobacterium breve* CNCM I-3865 (NCC2950) are non-replicating.

For this purpose the may be rendered non-replicating by any method known to those of skill in the art. The technologies described in the literature to render probiotic strains non-replicating include for example heat-treatments, irradiation, UV light or treatment by chemical agents, such as formalin or paraformaldehyde. Preferred are methods that require no addition of agents. In particular for preparations containing milk or milk compounds, heat treatments are preferred, since they are carried out anyway to reduce bacterial loads. This way, no extra process step will be required.

Non-replicating probiotic micro-organisms have the advantage that they are far easier to handle than their live counterparts. Additionally, they are more storage stable and need less stringent packaging conditions.

Non-replicating probiotic micro-organisms would allow to develop a large variety of functional foods which by their nature do not allow the addition of live probiotics without additional measures to protect them. This plays a role for example in the provision of cereal bars, fruit juices, UHT-drinks, shelf stable drinks, etc.

Furthermore, for example in immuno-compromised customers, the use of live probiotics might be limited due to a potential risk to develop bacteremia. Non-viable probiotics are also far better tolerated by immuno-compromised people.

Additionally, the provision of non-replicating probiotic micro-organisms allows the hot reconstitution, e.g., of powdered nutritional compositions.

"Non-replicating" means that no viable cells and/or colony forming units can be detected by classical plating methods. Such classical plating methods are summarized in the microbiology book: James Monroe Jay, Martin J. Loessner, David A. Golden. 2005. Modern food microbiology. 7th edition, Springer Science, New York, N.Y. 790 p. Typically, the absence of viable cells can be shown as follows: no visible colony on agar plates or no turbidity in liquid growth medium after inoculation with different concentrations of bacterial preparations ('non replicating' samples) and incubation under appropriate conditions (aerobic and/or anaerobic atmosphere for at least 24 h).

Prebiotics may be added to the composition. Prebiotics may support the growth of *Bifidobacterium breve* CNCM I-3865 (NCC2950). Prebiotics may also act synergistically with other viable probiotic bacteria, that may be present in the composition, or with beneficial bacteria in the intestine.

"Prebiotic" means non-digestible food substances that promote the growth of probiotics or health promoting microorganisms in the intestines. They are not broken down in the stomach and/or upper intestine or absorbed in the GI tract of the person ingesting them, but they are fermented by the gastrointestinal microbiota and/or by probiotics. Prebiotics are for example defined by Glenn R. Gibson and Marcel B. Roberfroid, Dietary Modulation of the Human Colonic Microbiota: Introducing the Concept of Prebiotics, J. Nutr. 1995 125: 1401-1412.

The prebiotics that may be used in accordance with the present inventions are not particularly limited and include all food substances that promote the growth of probiotics or health promoting microorganisms in the intestines. Preferably, they may be selected from the group consisting of oligosaccharides, optionally containing fructose, galactose, mannose; dietary fibers, in particular soluble fibers, soy fibers; inulin; or mixtures thereof. Preferred prebiotics are fructo-oligosaccharides (FOS), galacto-oligosaccharides (GOS), isomalto-oligosaccharides (IOS), xylo-oligosaccharides (XOS), oligosaccharides of soy, glycosylsucrose (GS), lactosucrose (LS), lactulose (LA), palatinose-oligosaccharides (PAO), malto-oligosaccharides (MOS), gums and/or hydrolysates thereof, pectins and/or hydrolysates thereof.

A further probiotic may be added to the composition.

Additional probiotics may be viable or non-replicating or a mixture of both. All probiotic micro-organisms may be combined with *Bifidobacterium breve* CNCM I-3865 (NCC2950). Preferably, such an added probiotic may be selected from the group consisting of the genera *Bifidobacterium, Lactobacillus, Lactococcus, Enterococcus, Streptococcus, Propionibacterium, Pediccoccus, Escherichia coil, Debaryomyces, Kluyveromyces, Saccharomyces, Schizosaccharomyces, Zygosaccharomyces, Yarrowia, Candida*, in particular selected from the group consisting of the species *Bifidobacterium longum, Bifidobacterium lactis, Bifidobacterium animalis, Bifidobacterium breve, Bifidobacterium infantis, Bifidobacterium bifidum, Bifidobacterium adolescentis, Lactobacillus acidophilus, Lactobacillus casei, Lactobacillus paracasei, Lactobacillus salivarius, Lactobacillus plantarum, Lactobacillus fermentum, Lactobacillus johnsonii, Lactobacillus reuteri, Lactobacillus gasseri, Lactobacillus rhamnosus, Lactococcus* ssp. such as *Lactococcus lactis, Lactococcus cremoris, Lactococcus diacetylactis, Enterococcus faecium, Enterococcus faecalis, Saccharomyces cerevisiae, Saccharomyces boulardii, Schizosaccharomyces pombe, Kluyveromyces lactis, Yarrowia lypolitica* or mixtures thereof, preferably selected from the group consisting of *Lactobacillus johnsonii* (NCC533; CNCM I-1225), *Bifidobacterium longum* (NCC490; CNCM I-2170), *Bifidobacterium longum* (NCC2705; CNCM I-2618), *Bifidobacterium longum* (NCC3001; ATCC BAA-999), *Bifidobacterium lactis* (NCC2818; CNCM I-3446), *Bifidobacterium breve* (strain A), *Lactobacillus paracasei* (NCC2461; CNCM I-116), *Lactobacillus rhamnosus* GG (ATCC53103), *Lactobacillus rhamnosus* LPR (NCC4007; CGMCC 1.3724), *Enterococcus faecium* SF 68 (NCIMB10415), and mixtures thereof. All these probiotics may be added in a viable or in a non-replicating form.

Food products according to the present invention include dairy products, such as fermented milk products, e.g. yoghurts, buttermilk, etc; ice creams; concentrated milk; milk; dairy creams; flavoured milk drinks; whey based drinks; toppings; coffee creamers; chocolate; cheese based products; soups; sauces; purees; dressings; puddings; custards; baby foods; nutritional formula, such as those for complete nutrition, e.g. for infants, children, teenagers, adults or the elderly; cereals and cereal bars.

Drinks include e.g. milk- or yoghurt based drinks, fermented milk, coffee, protein drinks, tea, energy drinks, soy drinks, fruit and/or vegetable drinks, fruit and/or vegetable juices.

Likewise, the composition may be administered orally, enterally and/or parenterally (for example: subcutaneous, intramuscular).

The composition of the present invention may further comprise a protein source, a carbohydrate source and or a lipid source.

For special clinical applications, in particular parenteral applications, it may be desirable to provide compositions which do not contain a carbohydrate source.

Since the allergen that triggers the allergic response is usually a food protein or a part thereof, the composition the protein source in compositions intended for allergic patients requires particular attention. In general, the type of protein present in the composition should not trigger allergic reactions. Hence the protein sources used may vary depending on the type of allergy that is to be prevented or treated by the composition of the present invention.

Any suitable dietary protein may be used, for example animal proteins (such as milk proteins, meat proteins and egg proteins) or hydrolysates thereof; vegetable proteins (such as soy protein, wheat protein, rice protein, and pea protein) or hydrolysates thereof; mixtures of free amino acids; or combinations thereof. Milk proteins such as casein and whey, and soy proteins or hydrolysates thereof may be preferred for some applications. If the protein source is a milk protein or a milk protein fraction, it may be for example sweet whey, acid whey, α-lactalbumin, β-lactoglobulin, bovine serum albumin, acid casein, caseinates, α-casein, β-casein, γ-casein. Of course combinations of different protein sources may be used.

As far as whey proteins are concerned, the protein source may be based on acid whey or sweet whey or mixtures thereof and may include α-lactalbumin and β-lactoglobulin in whatever proportions are desired. Preferably however, in particular if the composition is an infant feeding formula, the protein source is based on modified sweet whey. Sweet whey is a readily available by-product of cheese making and is frequently used in the manufacture of infant formulas based on cows' milk.

The proteins may be intact or hydrolysed or a mixture of intact and hydrolysed proteins. It may be desirable to supply extensively or partially hydrolysed proteins (degree of hydrolysis between 2 and 20%). The hydrolysis step may digest potential allergenic food proteins. Consequently, the provision of hydrolyzed proteins may be beneficial for allergic patients or people at risk of developing an allergy.

If hydrolysed proteins are required, the hydrolysis process may be carried out as desired and as is known in the art. For example, a whey protein hydrolysate may be prepared by enzymatically hydrolysing the whey fraction in one or more steps.

If the composition of the present invention contains a protein source, then the amount of protein or protein equivalent in the composition is typically in the range of 1.6-7.5 g/100 kcal of the composition.

In particular for nutritional formulas, the protein source should provide that the minimum requirements for essential amino acid content are met.

If the composition contains a carbohydrate source, the kind of carbohydrate to be used is not particularly limited. Any suitable carbohydrate may be used for example sucrose, lactose, glucose, fructose, corn syrup solids, maltodextrins, starch and mixtures thereof. Combinations of different carbohydrate sources may be used. The carbohydrates may preferably provide 30% to 80% of the energy of the composition. For example, the composition may comprise a carbohydrate source in an amount of 9-18 g/100 kcal of the composition.

If the composition contains a lipid source, the kind of lipid to be used is not particularly limited. If the composition includes a lipid source, the lipid source may provide 5% to 70% of the energy of the composition. Long chain n-3 and/or n-6 polyunsaturated fatty acids, such as DHA, ARA and/or EPA may be added. A suitable fat profile may be obtained using a blend of canola oil, corn oil, high-oleic acid sunflower oil and medium chain triglyceride oil. The composition may comprise a lipid source in an amount of 1.5-7 g/100 kcal of the composition.

The composition may also contain all vitamins and minerals understood to be essential in the daily diet and in nutritionally significant amounts. The presence and amounts of specific minerals and other vitamins will vary depending on the subject to be treated.

If necessary, the composition may contain emulsifiers and stabilisers such as soy lecithin, citric acid esters of mono- and di-glycerides, and the like.

The composition may optionally contain other substances which may have a beneficial effect such as fibres, lactoferrin, nucleotides, nucleosides, and the like.

The *Bifidobacterium breve* CNCM I-3865 (NCC2950) may be cultured according to any suitable method and prepared for addition to the composition by freeze-drying or spray-drying for example.

Additionally or alternatively, the live probiotic microorganisms may be provided in an encapsulated form.

It has been found that encapsulation of the bacteria has therapeutical and technical advantages. Encapsulation increases the survival of the bacteria and thus the number of live bacteria which arrive in the intestine. Furthermore, the bacteria are gradually released allowing a prolonged action of the bacteria on the health of the subject. Bacteria may be micro-encapsulated, for example as described by FR2443247 (Société des Produits Nestlé), incorporated herein by reference. Briefly, the bacteria may be freeze or spray dried and incorporated into a gel.

Those skilled in the art will understand that they can freely combine all features of the present invention described herein, without departing from the scope of the invention as disclosed. In particular, features described for the uses of the present invention may be applied to the composition of the present invention and vice versa.

Further advantages and features of the present invention will be apparent from the following Examples and Figures.

The invention claimed is:

1. A method for the treatment or prevention of allergic diarrhoea comprising the step of orally administering a composition comprising between $10^3$ and $10^{12}$ cfu of *Bifidobacterium breve* CNCM I-3865 (NCC2950) per g of the composition to an individual requiring same.

2. The method according to claim 1, wherein the composition is selected from the group consisting of a medicament, a therapeutic nutritional composition, an infant feeding formula, a follow-on formula, a growing-up milk, a food product, an animal food, a nutraceutical, a drink, and a food additive.

3. The method according to claim 1, wherein the composition comprises hydrolyzed proteins.

4. The method according to claim 1, wherein the composition comprises the *Bifidobacterium breve* CNCM I-3865 (NCC2950) in an amount equivalent to between $10^7$ and $10^{11}$ cfu/g of the composition.

5. The method according to claim 1, wherein in the composition at least 95% of the *Bifidobacterium breve* CNCM I-3865 (NCC2950) are non-replicating.

6. The method according to claim 1, wherein the composition comprises at least one prebiotic in an amount of from 0.3 to 6% by weight of the composition.

7. The method according to claim 1, wherein the composition is a supplement and comprises from $10^4$ to $10^{12}$ cfu of the *Bifidobacterium breve* CNCM I-3865 (NCC2950) per unit dose.

8. The method in accordance with claim 1 wherein the individual is an infant.

9. The method in accordance with claim 1 wherein the individual is a young child.

10. A method for treating allergic diarrhoea comprising orally administering a composition comprising between $10^3$ and $10^{12}$ cfu of *Bifidobacterium breve* CNCM I-3865 (NCC2950) per g of the composition to an individual having the allergic diarrhoea.

11. The method in accordance with claim 10, wherein the composition is in a form selected from the group consisting of a medicament, a therapeutic nutritional composition, an infant feeding formula, a follow-on formula, a growing-up milk, a food product, an animal food, a nutraceutical, a drink, and a food additive.

12. The method in accordance with claim 10 further comprising causing at least 95% of the *Bifidobacterium breve* CNCM I-3865 (NCC2950) to be non-replicating before administering the composition.

13. The method in accordance with claim 10 further comprising preparing the *Bifidobacterium breve* CNCM I-3865 (NCC2950) for addition to the composition by performing a step selected from the group consisting of freeze-drying the *Bifidobacterium breve* CNCM I-3865 (NCC2950), spray-drying the *Bifidobacterium breve* CNCM I-3865 (NCC2950), and encapsulating the *Bifidobacterium breve* CNCM I-3865 (NCC2950).

14. The method in accordance with claim 10 wherein the composition comprises hydrolyzed proteins.

15. The method in accordance with claim 10 wherein the individual is an infant.

16. The method in accordance with claim 10 wherein the individual is a young child.

* * * * *